United States Patent
Joo (10) Patent No.: US 8,382,931 B2
(45) Date of Patent: Feb. 26, 2013

(54) METHOD OF MANUFACTURING A CATHETER HAVING AN EXPANDABLE MEMBER

(75) Inventor: Don-Soo Joo, Gyeonggi-do (KR)

(73) Assignee: Imedicom Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/154,879

(22) Filed: Jun. 7, 2011

(65) Prior Publication Data

US 2012/0312448 A1 Dec. 13, 2012

(51) Int. Cl.
*B29C 65/04* (2006.01)

(52) U.S. Cl. ............... 156/272.2; 264/239; 264/405; 604/93.01

(58) Field of Classification Search ............ 156/272.2; 264/239, 405; 604/93.01
See application file for complete search history.

(56) References Cited

U.S. PATENT DOCUMENTS

| 5,714,110 A * | 2/1998 | Wang et al. ............ 264/529 |
| 5,811,506 A * | 9/1998 | Slagel ............ 528/64 |
| 2002/0098373 A1* | 7/2002 | Wang et al. ............ 428/542.8 |

* cited by examiner

*Primary Examiner* — Richard Crispino
*Assistant Examiner* — Elizabeth Royston
(74) *Attorney, Agent, or Firm* — Rabin & Berdo, P.C.

(57) ABSTRACT

A method for manufacturing a catheter includes preparing raw materials and maturing the raw materials in a drier at 50-55° C. for 20 days, preparing the expandable member, and the first and second tubes, in forms, by cutting the raw materials, fitting an index ring on the second tube, welding the expandable member to the first tube, and welding the expandable member with the second tube, connecting the first tube to a first side of the manifold, and connecting the second tube to a second side of the manifold, forming a shape and a size of the expandable member, and drying an interior of the expandable member and the second tube and maturing the expandable member for 24 hours in the drier at 50-55° C., then for 48 hours in the drier at 50-55° C.

3 Claims, 12 Drawing Sheets

| Electronic Document Version | TEST REPORT |

1. No : AT11-00257
2. Client
   - Name : IMEDICOM Co., LTD.
   - Address : 612, Hanlim Human Tower, 1-40, Guemjung-dong, Gunpo-si, Gyeonggi-do, Republic of Korea
   - Date of Receipt : Mar. 29, 2011
   - Date of Issued : Apr. 19, 2011
3. Test Sample : ① MEDINAUT Kyphoplasty System
   ② Kyphon Inflatable Bone Tamp & Osteo Introducer system
4. Test Results ------ Refer to the attached sheets ------

| Affirmation | Tested by Su Gil Hur  *S. G. Hur* | Technical Manager Gyoo-il Kang  *Kong G.I.* |

Our report apply only to the standards or procedures identified and to the sample(s) tested unless otherwise specified.
The test results are not indicative of representative of the qualities of the lot from which the sample was taken or of apparently identical or similar products.

Korea Conformity Laboratories president Tae Shik Oh  *TaeShik Oh*

Address : 406-841 7-44 Songdo-Dong, Yeonsu-Gu, Incheon, Korea  82-032-858-0011
Result Inquiry : Medical Device Evaluation Team  82-32-859-4065

FIG. 6B

TEST REPORT

No : AT11-00257

<Attached>

☐ Fatigue Test

1. Test Method : Product inspection procedure(Doc No. IM-BTP-01) by IMEDICOM co., Ltd.
   (Install the balloon catheter on the fatigue testing machine after injecting 5cc of distilled water using a syringe connected with a balloon catheter and repeat the dilation and contraction of balloon catheter for 100 times continuously.)

2. Test Sample : ① MEDINAUT Kyphoplasty system
   (Lot No. : CBB10082301)
   ② Kyphon Inflatable Bone Tamp & Osteo Introducer system
   (Lot No. : 01847777)

3. Test Results

| Test item | Requirements | Results ① | Results ② |
|---|---|---|---|
| Fatigue Test | Balloon catheter finished fatigue test shall not be damaged. | Conform | Conform |

- page 5 of 5 -

FIG. 6C

TEST REPORT

No : AT11-00257

<Attached>

☐ Bond Strength Test

1. Test Method : Product inspection procedure(Doc No. IM-BIP-01) by IMEDICOM co., Ltd.
   (Keep the pressure for 30 sec. with 350PSI(2.4MPa) after injecting distilled water using a syringe connected with a balloon catheter. Increase the pressure of balloon catheter under 350PSI(2.4MPa).)

2. Test Sample : ① MEDINAUT Kyphoplasty system
   (Lot No. : CBB10082301)
   ② Kyphon Inflatable Bone Tamp & Osteo Introducer system
   (Lot No. : 01847777)

3. Test Results

| Test item | Requirements | Results ① | Results ② |
|---|---|---|---|
| Fatigue Test | When the test condition keep the pressure for 30sec. with 350PSI(2.4MPa), 3-way cock, balloon tip and end using the bond shall not be damaged. | Conform | Conform |

------ End of Report ------

METHOD OF MANUFACTURING A CATHETER HAVING AN EXPANDABLE MEMBER

BACKGROUND

1. Field of the Invention

The invention relates to a method for manufacturing a catheter having an expandable member, which is for use in kyphoplasty.

2. Description of the Related Art

Patients with osteoporosis, and especially aged patients often experience severe pain at the back or waist area after being subjected to even a small impact. This is generally caused due to fracture, or compression fracture, which means that the weakened spinal bone is collapsed upon inflicted by the impact. Such pains are generally treated with vetebroplasty such as kyphoplasty.

The kyphoplasty is generally carried out in the following steps. First, a void is created with a spacer which is placed within a cannular inserted into an interior of a spinal bone, and a catheter having an expandable member is inserted into the spinal bone through the interior of the cannular. A cylinder device, which is connected to the catheter having expandable member, is then operated to expand the expandable member so that the body of the spinal bone is returned to the original form. Next, bone cement is injected into the void within the spinal bone which is created in accordance with the expansion of the expandable member. As a result, the spinal bone is restored to the original form.

Figure 1:
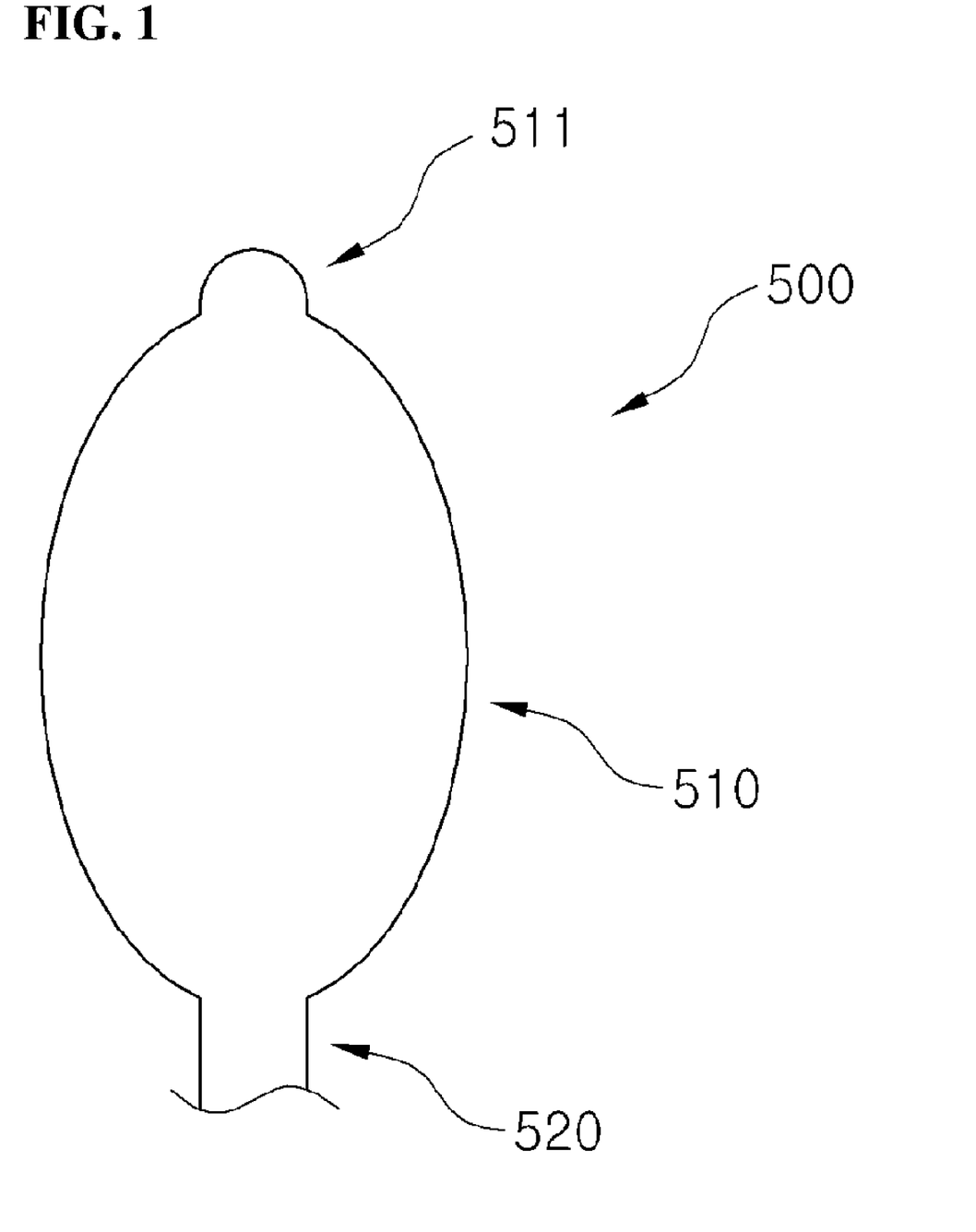
FIG. 1 is a conceptual view schematically illustrating an appearance of a conventional expandable member for use in a catheter.

FIG. 1 is a schematic view illustrating an appearance of a conventional expandable member of a catheter.

Referring to FIG. 1, the catheter having expandable member for use in kyphoplasty may have an undesirable deformation during shaping thereof. That is, in the conventional manufacturing process involving deposition and shaping of a first end 511 of the expandable member 510 with a first end of a second tube (not illustrated) formed within a first tube 520, the first end 511 of the expandable member 510 sometimes protrudes or overlaps with the second tube. Such deformation is undesirable, since when the catheter 500 having expandable member is inserted into the spinal bone in kyphoplasty, the protruding first end 511 of the expandable member 510 easily touches or is blocked by an inner wall of the void which is created by the spacer to receive the catheter 500 having expandable member. Therefore, to overcome the above-mentioned potential problem and ensure that the catheter 500 with the expandable member is inserted accurately, the void has to be created larger than necessary.

Furthermore, after the void is ensured by the expansion of the expandable member 510, the expandable member 510 on the first end of the catheter 500 having expandable member, which is thickened due to overlapping with the second tube within the first tube 520, can be blocked by the cannular while the catheter 500 is removed from the cannular.

Further, it is necessary that the expandable member 510 of the catheter 500 is made from a substance with effective hardness and elongation to be used in kyphoplasty. To be specific, high hardness and elongation are particularly necessary, which can endure sufficient supply of pressure, and at the same time, can permit sufficient expansion without having breakage, to ensure that the expandable member 510 expands the collapsed or dying bones. Conventionally, expandable members have been generally made from a substance containing duralyn which is a nylon family or silicone, and some polyurethane family, but these substances could not provide sufficient hardness and elongation to meet the need to expand the bones.

SUMMARY

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

According to one embodiment, a technical objective is to provide a method for manufacturing a catheter having an expandable member which enables safer and more efficient and accurate treatment with a catheter having the expandable member.

In one embodiment, a method for manufacturing a catheter having an expandable member may include steps of: preparing cylindrically-tubular raw materials for the expandable member, a first tube and a second tube to be passed through an interior of the first tube, with highly elastic thermoplastic polyurethane (TPU), maturing the raw materials in a drier at 50~55° C. for 20 days, so that the raw materials have 80~95 A of hardness, preparing the expandable member, the first tube and the second tube, in forms before being coupled to each other, by cutting the raw materials to lengths corresponding to the expandable member, the first tube and the second tube, respectively, heating the second tube with a hot air blower and fitting an index ring at a predetermined location of the second tube, contracting a diameter of a second end of the expandable member and welding the second end of the expandable member to a first end of the first tube using a high-frequency welding machine, and contracting a diameter of a first end of the expandable member and welding the first end of the expandable member with a first end of the second tube which is passed through the interior of the first tube using the high-frequency welding machine, connecting a second end of the first tube to a first side of a manifold, and connecting a second end of the second tube to a second side of the manifold, forming a shape and a size of the expandable member using a molding machine and a mold, drying an interior of the expandable member and the second tube and maturing the expandable member for 24 hours in the drier at 50~55° C., conducting a pressure test in which the expandable member is subjected to maximum 350 psi of pressure, a welding inspection between the expandable member and the first tube, and between the expandable member and the second tube, and an inspection of connected state between the manifold and the first tube, and between the manifold and the second tube, and drying the interior of the expandable member and the second tube and maturing the expandable member for 48 hours in the drier at 50~55° C.

The index ring may be made from a radiopaque material, and the predetermined location may correspond to the first end and the second end of the expandable member respectively for prediction of the location of the expandable member through the index ring.

The contracting may include steps of: contracting the diameter of the second end of the expandable member by heating approximately 5 mm range from the second end of the expandable member with the high-frequency welding machine for approximately three seconds, inserting the first end of the first tube within 5 mm in depth of the second end of the expandable member, and connecting the first end of the first tube with the second end of the expandable member by welding with the high-frequency welding machine, contracting the diameter of the first end of the expandable member by heating approximately 5 mm range from the first end of the expandable member with the high-frequency welding machine for approximately 3 seconds, and passing the second tube through the interior of the first tube, and connecting the first end of the second tube with the first end of the expandable member by welding with the high-frequency welding machine.

According to an embodiment, by applying highly elastic TPU for the expandable member, and maturing the material according to predetermined repeated steps, the properties of the highly elastic TPU can be enhanced to optimize the hardness and elongation of the expandable member. As a result, more effective and precise treatment is possible by using the catheter having expandable member.

Further, in addition to the use of the above-mentioned materials and processing steps, the use of high-frequency welding machine for deposition can prevent protrusion or overlapping of the first end of the expandable member, which was a problematic phenomenon in the conventional art. Accordingly, the catheter having expandable member can be inserted to an intended location with accuracy, without requiring a sufficient room for the corresponding space. As a result, safer and more effective and accurate treatment is possible.

Further, since the index rings made from a radiopaque material such as platinum are arranged at predetermined locations of the second tube which correspond to the first end and the second end of the expandable member, the precise location and range of the expandable member can be checked by X-ray during a treatment using the catheter having expandable member.

BRIEF DESCRIPTION OF THE DRAWINGS

The above and/or other aspects of the present inventive concept will be more apparent by describing certain exemplary embodiments of the present inventive concept with reference to the accompanying drawings, in which.

DETAILED DESCRIPTION OF EXEMPLARY EMBODIMENTS

Certain exemplary embodiments of the present inventive concept will now be described in greater detail with reference to the accompanying drawings.

In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters. Also, well-known functions or constructions are not described in detail since they would obscure the invention with unnecessary detail.

Figure 2:
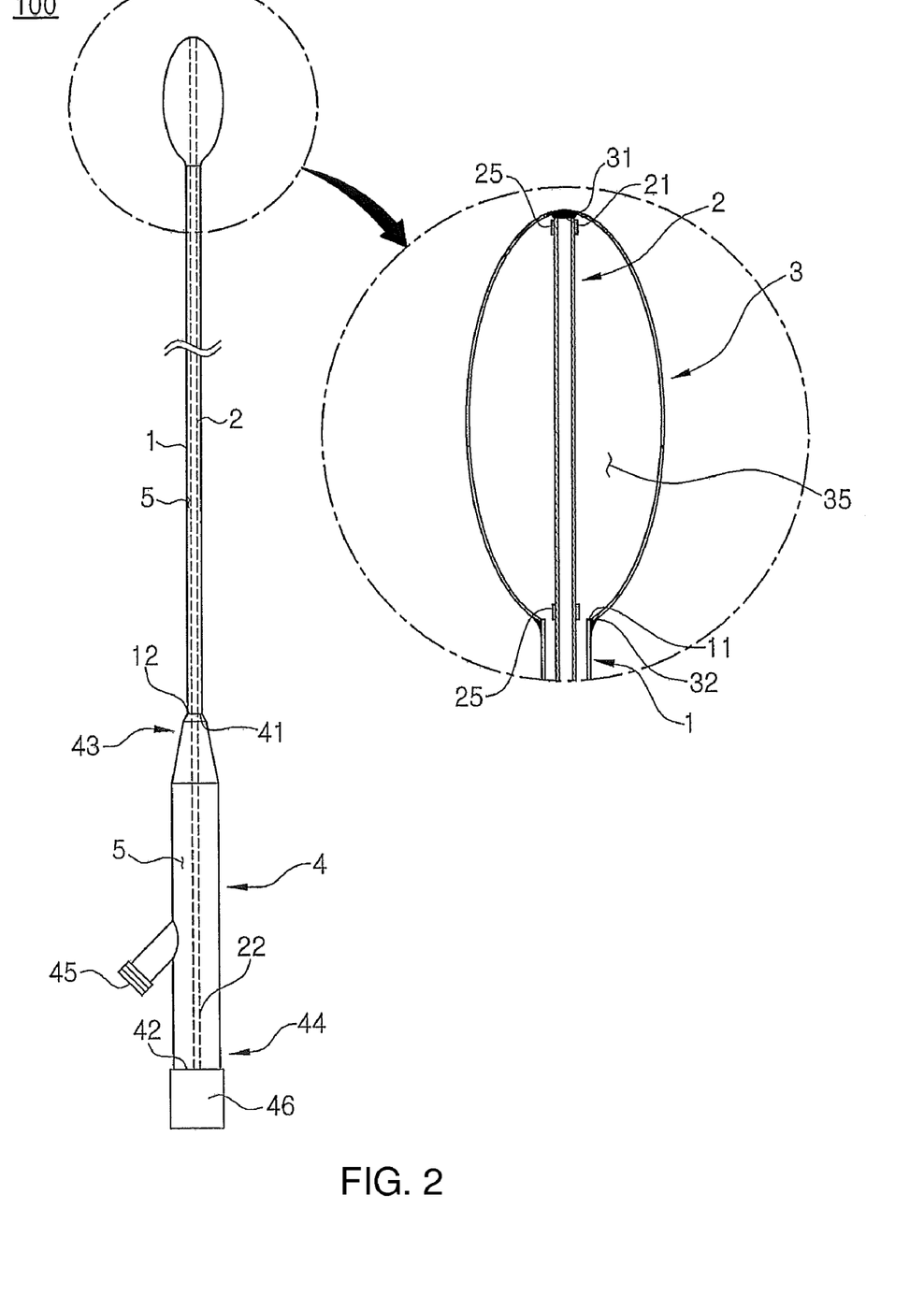
FIG. 2 is a schematic view illustrating a catheter having an expandable member manufactured by a method for manufacturing a catheter having an expandable member, according to an embodiment.
Figure 3:
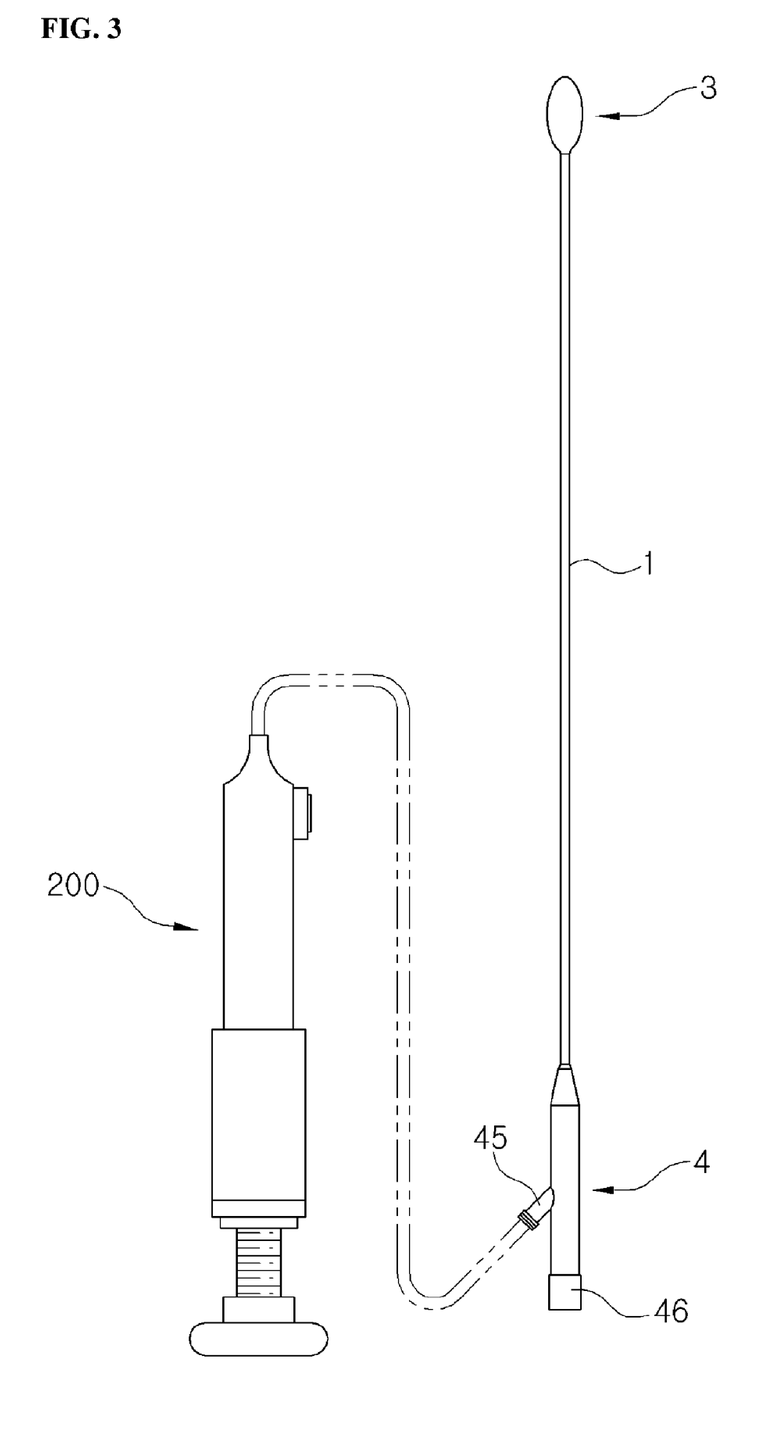
FIG. 3 is a schematic view illustrating the catheter having expandable member of FIG. 2 connected to a cylinder device during use.

FIG. 2 is a schematic view illustrating a catheter having an expandable member manufactured by a method for manufacturing a catheter having an expandable member, according to an embodiment, and FIG. 3 is a schematic view illustrating the catheter having expandable member of FIG. 2 connected to a cylinder device during use.

First, a catheter having an expandable member which is manufactured by a method for manufacturing a catheter having an expandable member according to an embodiment (hereinbelow, shortly 'catheter 100 having expandable member') will be explained.

Among many equipments used for kyphoplasty to surgically treat spine, the catheter 100 having expandable member is used to expand a curvature within a spinal bone during surgery to treat fracture, necrosis or dent in the spine. The catheter 100 having expandable member expands the curvature within spinal bone using expansion of the expandable member 3, to thus permit bone cement to be injected into the expanded curvature and restore the debilitated and deformed spine. Since the expandable member 3 is expanded by pneumatic or fluidic pressure transmitted thereto by a cylinder device 200 (see FIG. 3), the expandable member 3 needs to have a sufficient degree of hardness and elongation to expand the curvature within the spinal bone.

Referring to FIGS. 2 and 3, the catheter 100 having expandable member may include the expandable member 3, a first tube 1 and a second tube 2. The catheter 100 having expandable member may additionally include a manifold 4.

Referring to FIG. 2, the first tube 1 is formed as a cylindrical tube, in which a first end 11 is welded to a second end 32 of the expandable member 3. Further, the second tube 2 is arranged across an interior of the first tube 1, and formed as a cylindrical tube with a smaller diameter than that of the first tube 1. FIG. 2 shows the first end 21 of the second tube 2 welded to the first end 31 of the expandable member 3.

The manifold 4 may include an introducing port 45 which may be connected to the cylinder device 200 to receive fluid. By way of example, and referring to FIGS. 2 and 3, the introducing port 45 may be formed on a first side of the manifold 4. A removable cap 46 may be formed on a second end 42 of the manifold 4. By way of example, the cap 46 may have a threshold formed on an inner circumference to be screw-coupled with the second end 42 of the manifold 4.

The second end 12 of the first tube 1 may be connected to the first side 43 of the manifold 4. By way of example, the second end 12 of the first tube 1 may be assembled by being inserted into a first end 41 of the manifold 4, and thus connected to the first side 43 of the manifold 4. Additionally, the second tube 2 may be arranged within the first tube 1, with the second end 22 being connected to a second side 44 of the manifold 4.

Further, the second tube 2 may include an index ring 25. By way of example, the index ring 25 may have an annular configuration. Further, when an inner diameter of the second tube 2 is expanded by hot air, the index rings 25 may be respectively fitted around the first end 21 of the second tube 2 and around a portion (near to the first end 11 of the first tube 1) which is at a predetermined distance (i.e., approximately corresponding to the length of the expandable member 3) away from the first end 21.

The index ring 25 may be made from a radiopaque material (e.g., platinum) to enable checking of accurate location and range of the expandable member 3 by X-ray during treatment using the catheter 100 having expandable member.

Referring to FIG. 2, by the incorporation of the elements 1, 2, 3, 4, a fluid introducing space 5 is formed between the first tube 1 and the second tube 2. That is, fluid introduced through the introducing port 45 of the manifold 4 from the cylinder device 200 may pass through the fluid introducing space 5 between the first tube 1 and the second tubes 2 and advance to the expandable member 3. Since the second end 22 of the second tube 2 is connected (e.g., adhered) to an inner circumference of the second side 44 of the manifold 4 (see FIG. 2), the fluid is introduced only into the fluid introducing space 5 formed between the first tube 1 and the second tube 2, while not being introduced into the first tube 1.

Further, as explained above, since the first end 31 and the second end 32 of the expandable member 3 are welded to the first tube 1 and the second tube 2 respectively, the interior of the expandable member 3 is sealed off from the outside to thereby define an expandable space 35 which is expandable by the fluid introduced through the fluid introducing space 5.

Figure 4:
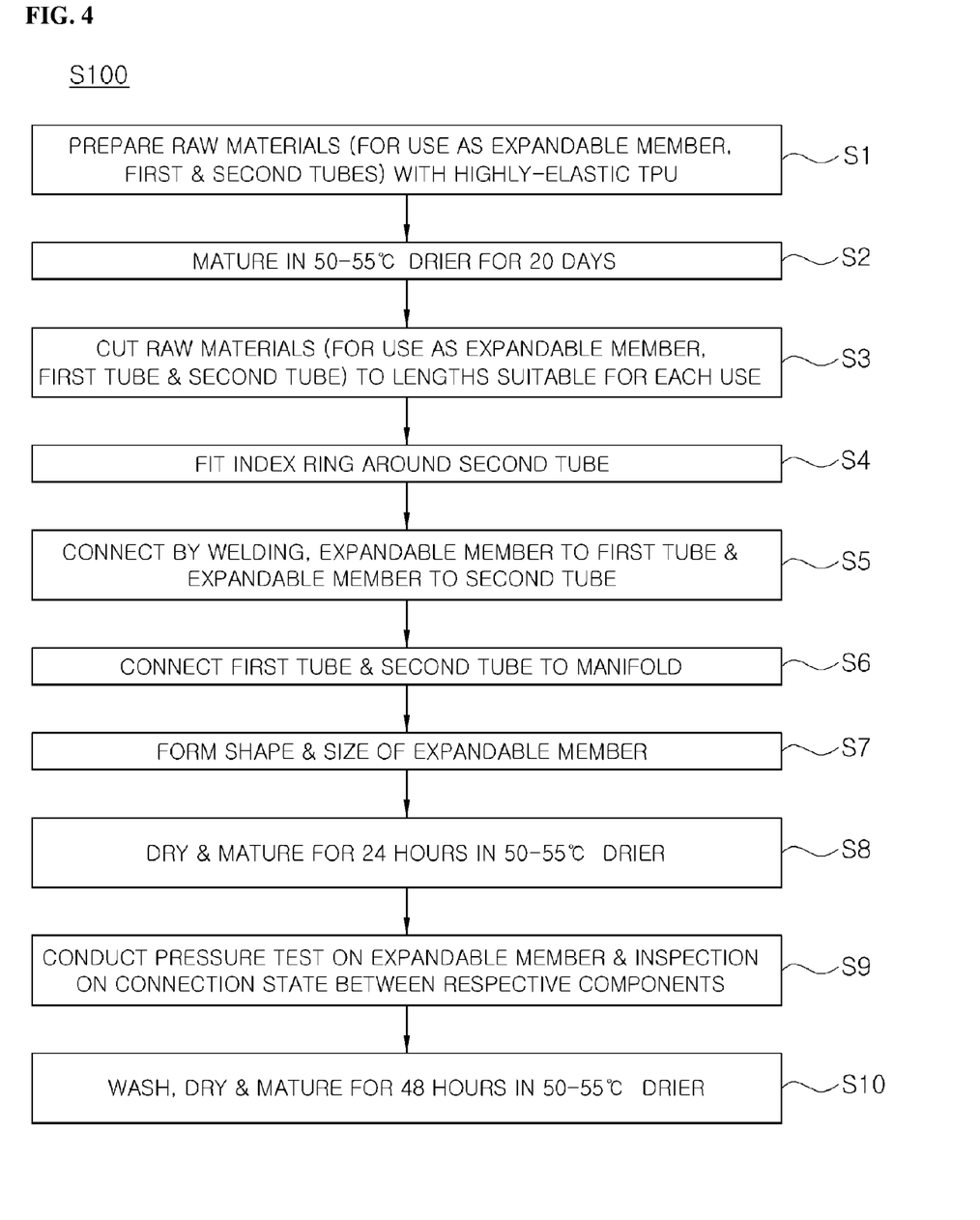
FIG. 4 is a flowchart provided to explain a method for manufacturing a catheter having an expandable member, according to an embodiment.

Meanwhile, FIG. 4 is a flowchart provided to explain a method for manufacturing a catheter having an expandable member, according to an embodiment, and FIGS. 5A to 5E are schematic views provided to explain welding steps of a method for manufacturing a catheter having an expandable member, according to an embodiment.

A method (S100, shortly 'method for manufacturing catheter having expandable member') for manufacturing a catheter having an expandable member according to an embodiment, which is used to manufacture the catheter 100 having expandable member explained above, will be explained below.

Referring to FIG. 4, the method (S100) for manufacturing a catheter having expandable member may include a step (S1) of preparing cylindrically-tubular raw materials for the expandable member 3, the first tube 1 and the second tube 2 to be passed through the interior of the first tube 1, with highly elastic thermoplastic polyurethane (TPU), in which the cylindrically-tubular raw materials each have a corresponding inner diameter to the expandable member 3, and the first and second tubes 1, 2.

At S1, the cylindrically-tubular raw materials of highly elastic TPU may be prepared respectively for use as the expandable member 3, and the first and second tubes 1, 2. By way of example, the raw material for use as the expandable member 3 may be prepared to a diameter of 4.0 mm, and the raw materials for use as the first and second tubes 1, 2 may be prepared to diameters of 3.2 mm and 1.6 mm, respectively.

The highly elastic TPU, which is used as the substance for the raw materials of the expandable member 3 and the first tube 1 and the second tube 2, are rubber-phase elastic polymers chemically having regular urethane functional group (—NH—CO—O—) in the molecular structure, which are used in a wide range of industries such as coating materials, elastic textile, sealant or the like. The highly elastic TPU particularly has superior wear resistance, flexibility and tensile strength.

Further, referring to FIG. 4, the method (S100) for manufacturing a catheter having expandable member may include a step (S2) of maturing the raw material in a drier (not illustrated) at 50~55° C. for 20 days, so that the raw materials have a fixed physical property of 80~95 A of hardness. That is, S2 is carried out in consideration of the fact that it is most effective when the expandable member 3 has hardness ranging between 80~95 A based on the hardness of soft materials (in Shore A) which does not affect the bone.

Accordingly, at S2, the raw materials for use as the expandable member 3, and the first and second tubes 1, 2 may be matured under predetermined temperature and time conditions to have the hardness ranging between 80~95 A as the invariable physical property.

Referring again to FIG. 4, the method (S100) for manufacturing a catheter having expandable member may include a step (S3) of preparing expandable member 3, first tube 1 and second tube 1, in forms before being coupled to each other, by cutting the raw materials to lengths corresponding to the expandable member 3, the first tube 1 and the second tube 2. In other words, at S3, the raw materials prepared for use as the expandable member 3, the first tube 1 and the second tube 2 may be cut to lengths that suit respective uses. By way of example, the raw material for use as the expandable member 3 may be cut to 25 mm, the raw material for use as the first tube 1 may be cut to 235 mm, and the raw material for use as the second tube 2 may be cut to 310 mm in length, respectively. By cutting, the expandable member 3, the first tube 1 and the second tube 2 can be individually prepared to the forms before coupling with each other.

For reference, although the individually-prepared components 1, 2, 3 are closer to the state of raw materials, for the purpose of convenience of explanation, the raw materials will be respectively called the 'expandable member 3', 'first tube 1' and 'second tube 2' after when these are set to have appropriate diameters and lengths.

Further, referring to FIG. 4, the method (S100) for manufacturing a catheter having expandable member may include a step (S4) of heating the second tube 2 with a hot air blower (not illustrated) and then fitting index rings 25 at predetermined locations of the second tube 2.

The 'predetermined locations of the second tube 2' may the locations corresponding to the first and second ends 31, 32 of the expandable member 3 for prediction of the location of the expandable member 3 through the index rings 25. For example, the length of the expandable member 3 may be 10 mm, 15 mm, or 20 mm, and the index rings 25 may preferably be fitted at locations according to the length of the expandable member 3 to enable more precise prediction of the range of the expandable member 3.

By way of example, referring to FIG. 2, when an inner diameter of the second tube 2 is expanded by hot air, the index rings 25 may be respectively fitted around the first end 21 of the second tube 2 and around a portion (near to the first end 11 of the first tube 1) which is at a predetermined distance (i.e., approximately corresponding to the length of the expandable member 3) away from the first end 21.

The index ring 25 may be made from a radiopaque material (e.g., platinum). By doing so, it is possible to check accurate location and range of the expandable member 3 by X-ray during treatment using the catheter 100 having expandable member.

Further, referring to FIG. 4, the method (S100) for manufacturing a catheter having expandable member may include a step (S5) of contracting a diameter of the second end 32 of the expandable member 3 and welding the second end 32 of the expandable member 3 to the first end 11 of the first tube 1 by using a high-frequency welding machine (not illustrated), and contracting the diameter of the first end 31 of the expandable member 3 and welding the first end 31 of the expandable member 3 with the first end 21 of the second tube 2 which is passed through the interior of the first tube 1 by using the high-frequency welding machine (not illustrated).

Figure 5A:
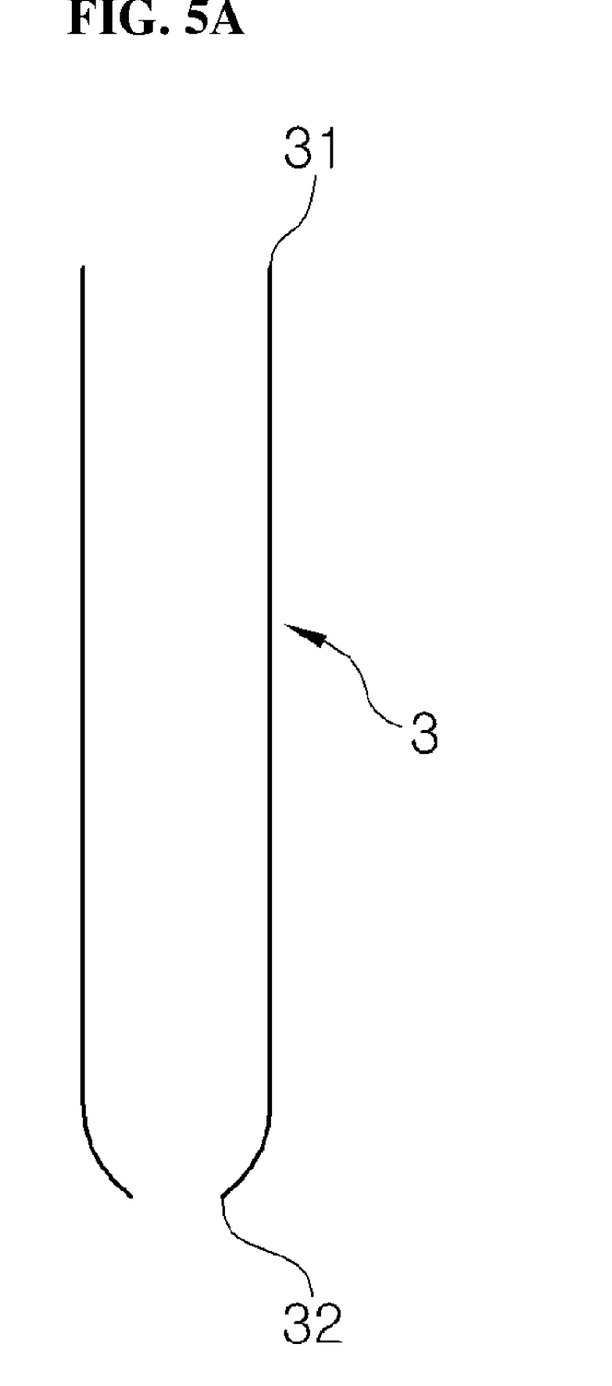
FIGS. 5A to 5E are schematic views provided to explain welding steps of a method for manufacturing a catheter having an expandable member, according to an embodiment.
Figure 5B:
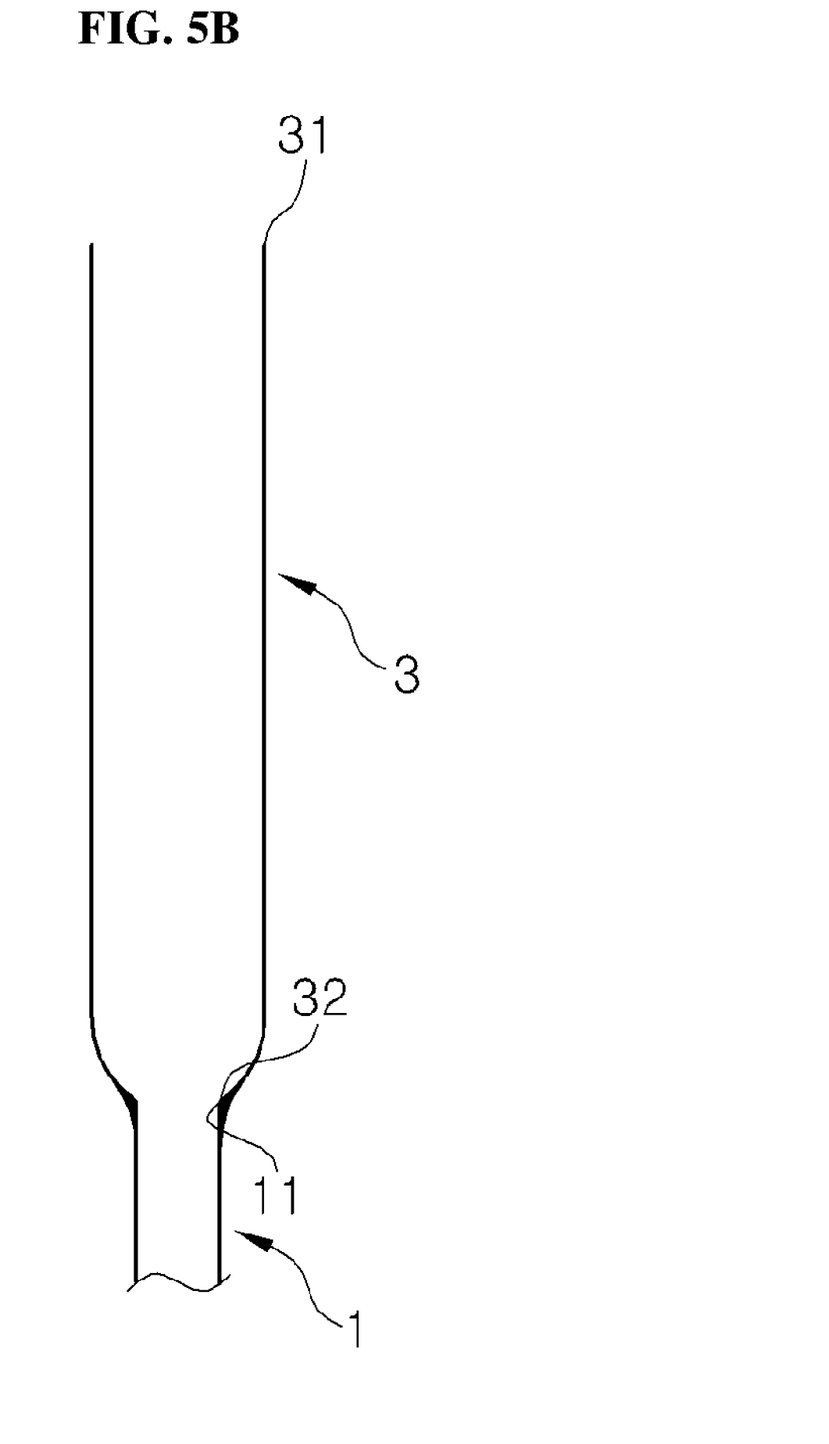
Figure 5C:
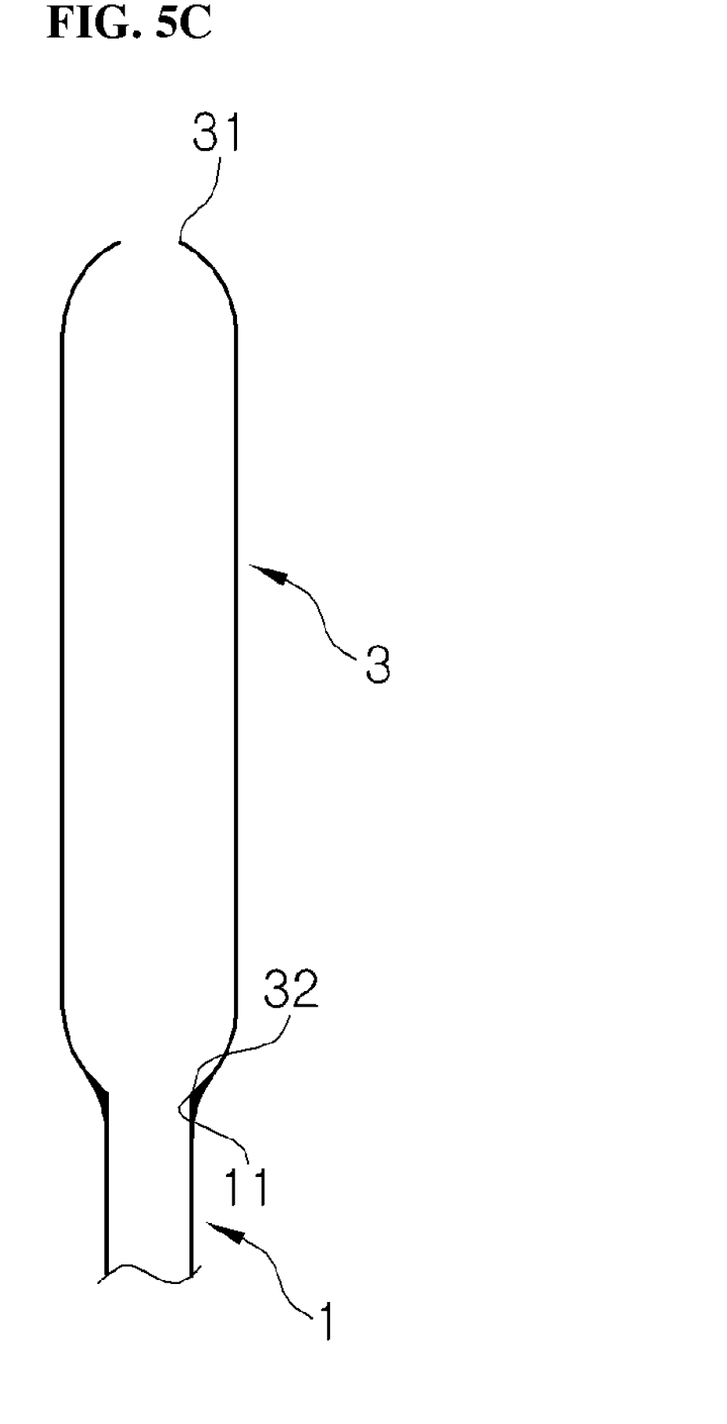
Figure 5D:
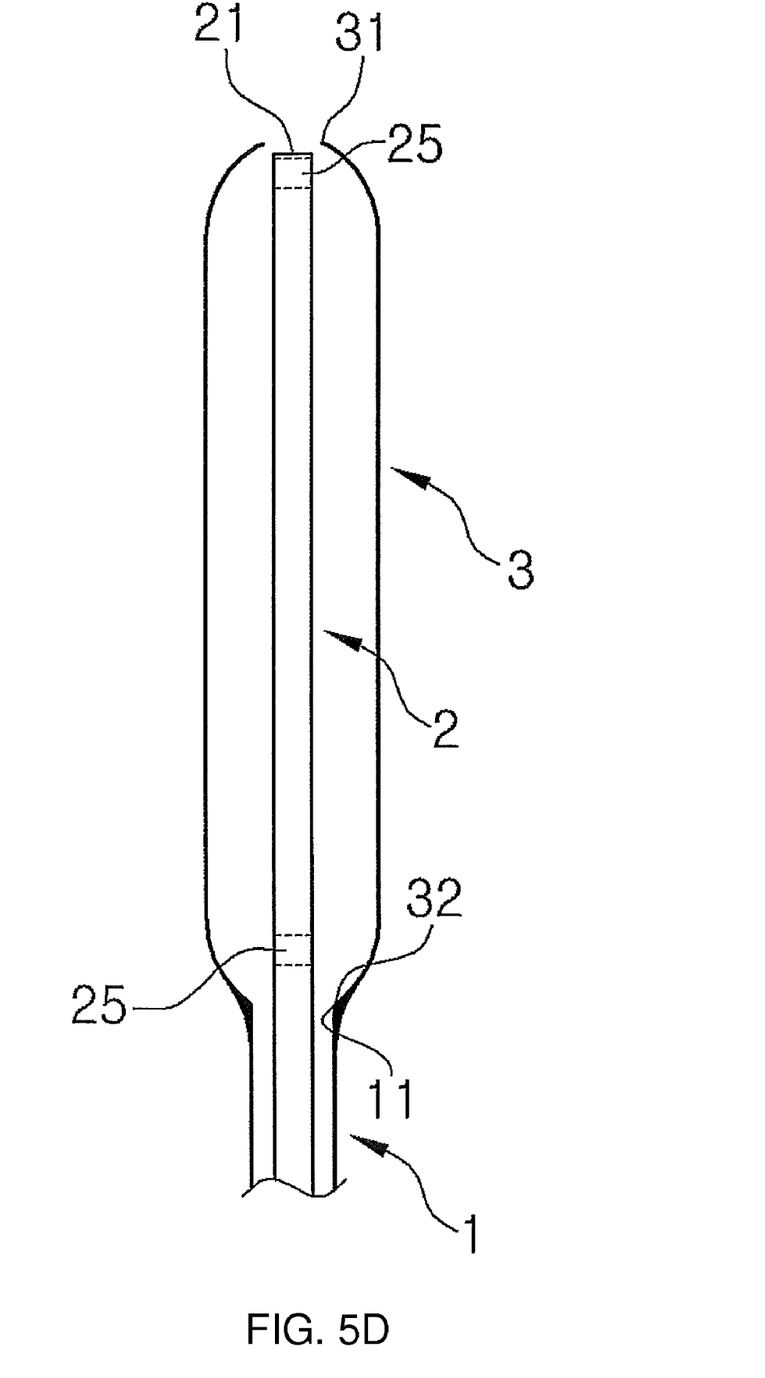
Figure 5E:
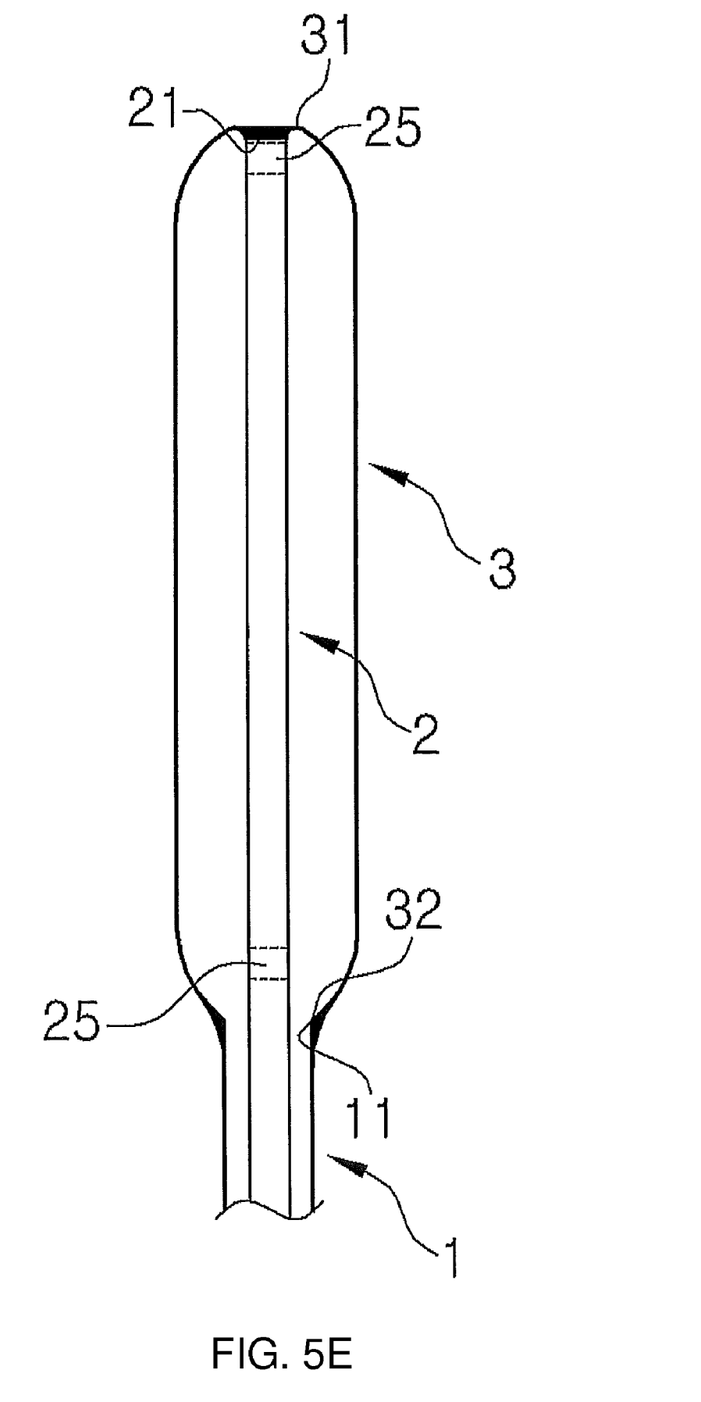

By way of example, referring to FIGS. 5A to 5E, the step (S5) may include steps of: contracting a diameter of the second end 32 of the expandable member 3 by heating approximately 5 mm range from the second end 32 of the expandable member 3 with the high-frequency welding machine for approximately three seconds (see FIG. 5A); inserting the first end 11 of the first tube 1 within 5 mm in depth of the second end 32 of the expandable member 3, and connecting the first end 11 of the first tube 1 with the second end 32 of the expandable member 3 by welding with the high-frequency welding machine (see FIG. 5B); contracting a diameter of the first end 31 of the expandable member 3 by heating approximately 5 mm range from the first end 31 of the expandable member 3 with the high-frequency welding machine for approximately 3 seconds (see FIG. 5C); and passing the second tube 2 through the interior connecting the expandable member 3 and the first tube 1, and connecting the first end 21 of the second tube 2 with the first end 31 of the expandable member 3 by welding with the high-frequency welding machine (see FIGS. 5D and 5E).

Further, referring to FIG. 4, the method (S100) for manufacturing a catheter having expandable member may include a step (S6) of connecting the second end 12 of the first tube 1 to the first side 43 of the manifold 4 (by assembling, for example), and connecting the second end 22 of the second tube 2 to the second side 44 of the manifold 4 (by adhesion, for example).

Further, referring to FIG. 4, the method (S100) for manufacturing a catheter having expandable member may include a step (S7) of forming a shape and a size of the expandable member 3 using a molding machine and a mold (not illustrated).

By way of example, the length of the expandable member 3 may be 10 mm, 15 mm, or 20 mm, and at the molding step (S7), the shape and size of the expandable member 3 may preferably molded depending on the length thereof.

Further, referring to FIG. 4, the method (S100) for manufacturing a catheter having expandable member may include a step (S8) of drying the interior of the expandable member 3 and the second tube 2, and maturing the expandable member 3 for 24 hours in the drier at 50~55° C. For example, at S8, the expandable member 3, the first tube 1, the second tube 2 and the manifold 4 may be dried and matured for 24 hours in the drier at 50~55° C.

Further, referring to FIG. 4, the method (S100) for manufacturing a catheter having expandable member may include a step (S9) of conducting pressure test in which the expandable member 3 is subjected to maximum 350 psi of pressure, welding inspection between the expandable member 3 and the first tube 1, and between the expandable member 3 and the second tube 2, and inspection of connected state (e.g., assembling, adhesion, or the like) between the manifold 4 and the first tube 1, and between the manifold 4 and the second tube 2. At S9, inspection for the deficiencies other than pressure, welding, assembling, or adhesion state, may also be conducted.

Further, referring to FIG. 4, the method (S100) for manufacturing a catheter having expandable member may include a step (S10) of drying the interior of the expandable member 3 and the second tube 2 and maturing the expandable member 3 for 48 hours in the drier at 50~55° C. For example, at S10, the expandable member 3, the first tube 1, the second tube 2 and the manifold 4 may be dried and matured for 24 hours in the drier at 50~55° C.

Accordingly, by the respective steps of the method (S100) for manufacturing a catheter having expandable member, the catheter 100 having expandable member for use in kyphoplasty, which is made from highly elastic TPU and has optimum hardness and elongation, can be prepared.

That is, according to the method (S100) for manufacturing a catheter having expandable member, by using highly elastic TPU as the raw materials and repeatedly maturing the raw materials at predetermined temperature for predetermined period (S2, S8, S10), the catheter 100 having expandable member having optimum hardness and elongation can be manufactured. Accordingly, the expandable member 3 of the catheter 100 having expandable member manufactured in the manner as explained above, can have superior durability against internal expansion pressure and be effectively used to create a space within a bone without affecting the bone.

Figure 6A:
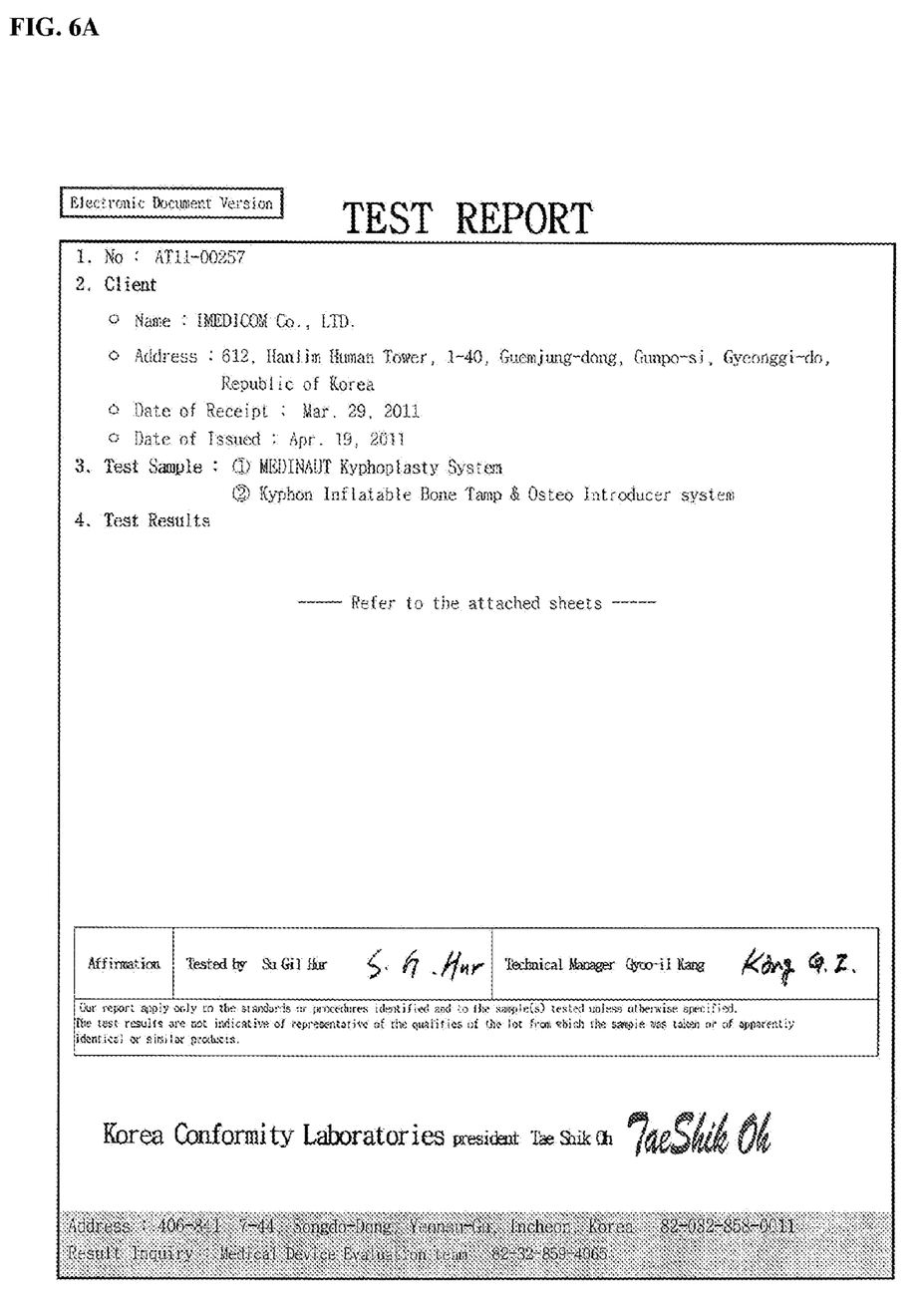
FIGS. 6A to 6C are views illustrating results of fatigue test and bone hardness test issued by an authority regarding a catheter having a expandable member which is manufactured by a method for manufacturing a catheter having an expandable member according to an embodiment.
Figure 6B:
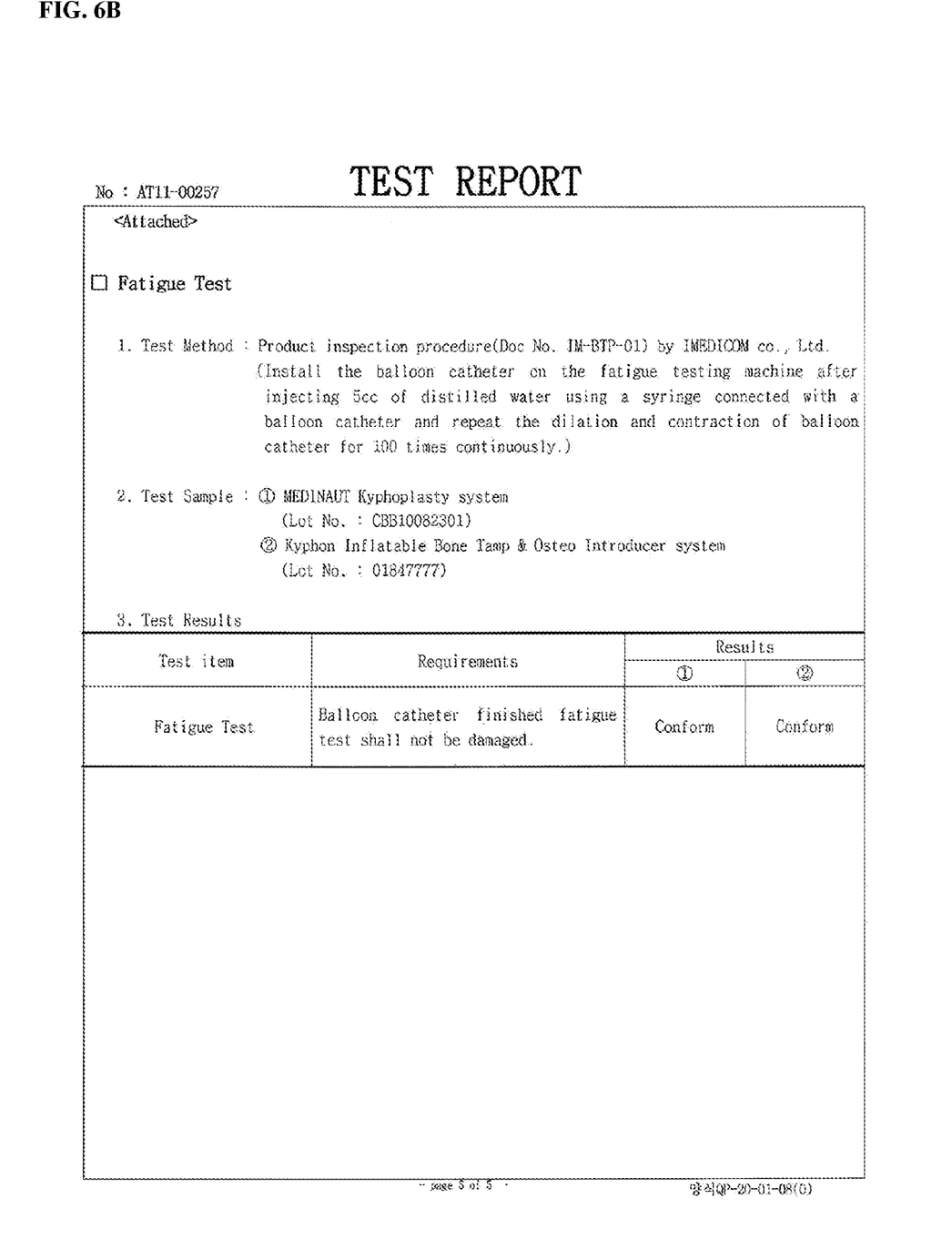
Figure 6C:
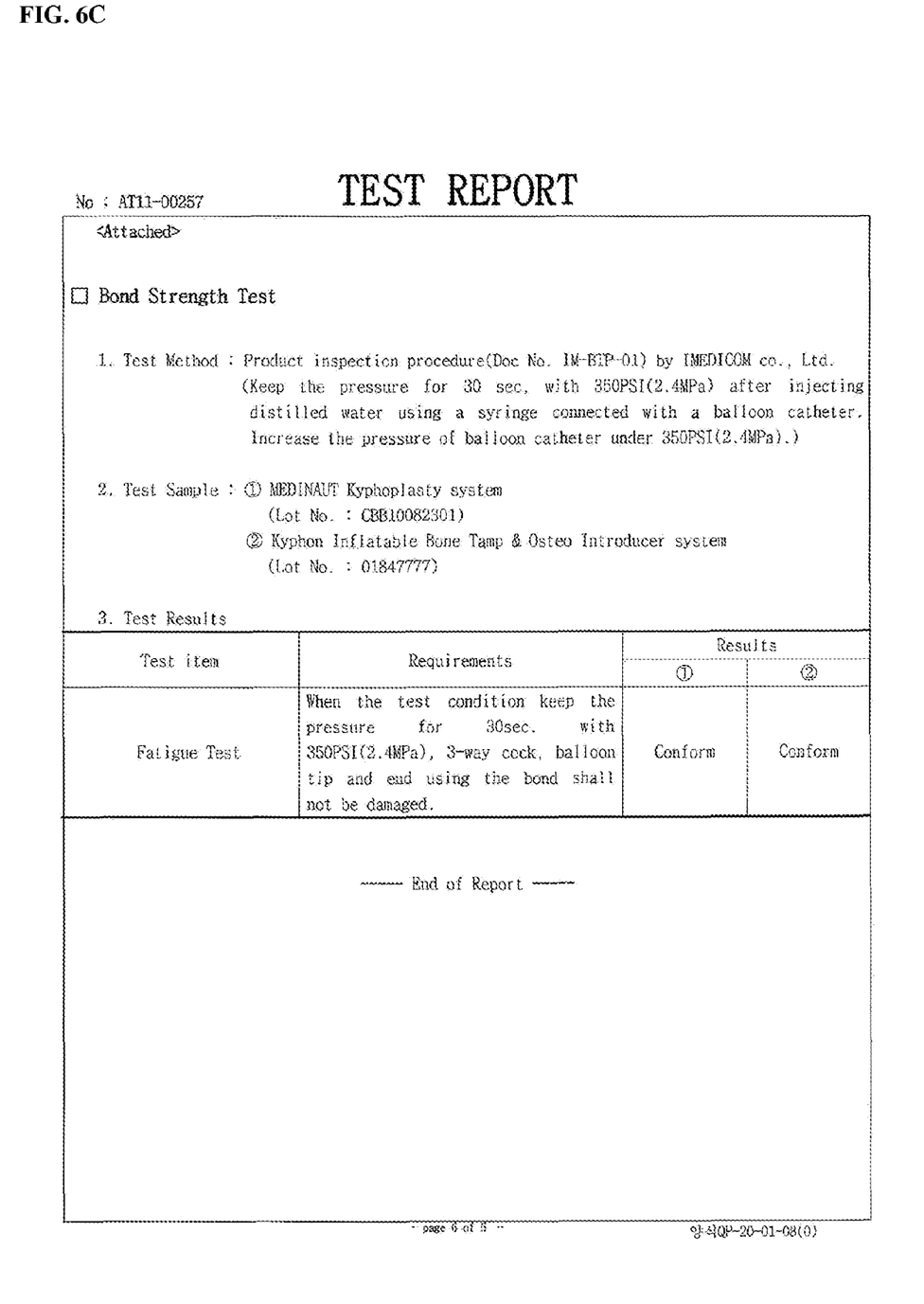

FIGS. 6A to 6C are views illustrating results of fatigue test and bone hardness test issued by an authority regarding a catheter having a expandable member which is manufactured by a method for manufacturing a catheter having an expandable member according to an embodiment. In other words, FIGS. 6A to 6C illustrate the results of tests conducted by the related authority to determine whether the catheter 100 having expandable member, which is manufactured by the method (S100) for manufacturing a catheter having expandable member, i.e., by using highly elastic TPU, welding with the high-frequency welding machine, and repeating predetermined maturing steps, have achieved optimum hardness and elongation.

Referring to FIG. 6B, a syringe was connected to the catheter 100 having expandable member, distilled water was injected therethrough, the catheter 100 having expandable member was placed in the fatigue tester, and then the fatigue test was conducted by repeating expansion and contraction of the expandable member 3 for 100 times. The catheter 100 having expandable member was not damaged even when the fatigue test was completed.

Referring to FIG. 6C, a syringe was connected to the catheter 100 having expandable member, distilled water was injected therethrough, and then the adhesiveness test was conducted by maintaining 350 psi of pressure for 30 seconds. As shown, the welding portions of the first and second ends 31, 32 of the expandable member 3 of the catheter 100 having expandable member were not damaged after completion of the adhesiveness test. Accordingly, it was confirmed that the catheter 100 having expandable member has ensured a predetermined required adhesiveness, by the deposition through the high-frequency welding machine.

According to the present invention, by applying highly elastic TPU for the expandable member 3, and maturing the material according to predetermined repeated steps, the properties of the highly elastic TPU can be enhanced to optimize the hardness and elongation of the expandable member 3. As a result, more effective and precise treatment is possible using the catheter 100 having expandable member according to an embodiment.

Further, in addition to the use of the above-mentioned materials and processing steps, the use of high-frequency welding machine for deposition can prevent protrusion or overlapping of the first end of the expandable member 3, which was a problematic phenomenon in the conventional art. Accordingly, the catheter 100 having expandable member can be inserted to an intended location with accuracy, without requiring a sufficient room for the corresponding space. As a result, safer and more effective and accurate treatment is possible.

Further, since the index rings 25 made from a radiopaque material (e.g., platinum) are arranged at predetermined locations of the second tube 2 which correspond to the first end 31 and the second end 32 of the expandable member 3, the precise location and range of the expandable member 3 can be checked by X-ray during a treatment using the catheter 100 having expandable member.

The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, and not to limit the scope of the claims, and many alternatives, modifications, and variations will be apparent to those skilled in the art.

What is claimed is:

1. A method for manufacturing a catheter having an expandable member, the method comprising steps of:
   preparing cylindrically-tubular raw materials from highly elastic polyurethane (TPU) including an expandable member with a first and second end, a first tube with a first and second end, and a second tube with a first and second end, where the second tube is passed through an interior of the first tube;
   maturing said raw materials in a drier at 50-55° C. for 20 days, so that said raw materials have 80-95A of hardness;
   preparing said expandable member, said first tube and said second tube into forms for coupling to each other by cutting said raw materials to lengths corresponding to said expandable member, said first tube and said second tube, respectively;
   heating said second tube with a hot air blower and fitting index rings to said second tube at predetermined locations;
   contracting a diameter of said second end of said expandable member and welding said second end of said expandable member to said first end of said first tube using a high-frequency welding machine, and contracting a diameter of said first end of said expandable member and welding said first end of said expandable member with said first end of the second tube which is passed through the interior of said first tube using the high-frequency welding machine;
   connecting said second end of said first tube to a first side of a manifold, and connecting said second end of said second tube to a second side of the manifold;
   forming said expandable member to a shape and a size using a molding machine and a mold;
   drying an interior of said expandable member and said second tube and maturing said expandable member for 24 hours in the drier at 50-55° C.;
   conducting a pressure test in which said expandable member is subjected to a maximum pressure of 350 psi;
   conducting a welding inspection between said expandable member and said first tube, and between said expandable member and said second tube;
   conducting an inspection of the connected state between said manifold and said first tube, and between said manifold and said second tube; and
   drying the interior of said expandable member and said second tube and maturing said expandable member for 48 hours in the drier at 50-55° C.

2. The method of claim 1, wherein said index rings are made from a radiopaque material, and the predetermined locations correspond to said first end and said second end of said expandable member respectively, permitting the prediction of the location of the expandable member via the index rings.

3. The method of claim 1, wherein the contracting step comprises:
   contracting the diameter of said second end of said expandable member by heating an approximately 5 mm range from said second end of said expandable member with a high-frequency welding machine for approximately three seconds;
   inserting said first end of said first tube into said second end of said expandable member to within a 5 mm depth, and connecting said first end of said first tube with said second end of said expandable member by welding with said high-frequency welding machine;
   contracting the diameter of said first end of said expandable member by heating an approximately 5 mm range from said first end of said expandable member with said high-frequency welding machine for approximately 3 seconds; and
   passing said second tube through the interior of said first tube, and connecting said first end of said second tube with said first end of said expandable member by welding with said high-frequency welding machine.

* * * * *